United States Patent
Niwa (10) Patent No.: US 9,155,648 B2
(45) Date of Patent: Oct. 13, 2015

(54) STENT DELIVERY SYSTEM AND METHOD USING THE SAME

(71) Applicant: Terumo Kabushiki Kaisha, Tokyo (JP)

(72) Inventor: Takako Niwa, Bunkyou-ku (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/188,498

(22) Filed: Feb. 24, 2014

(65) Prior Publication Data

US 2014/0172114 A1 Jun. 19, 2014

Related U.S. Application Data

(62) Division of application No. 13/401,185, filed on Feb. 21, 2012, now abandoned.

(30) Foreign Application Priority Data

Mar. 24, 2011 (JP) .................. 2011-066755

(51) Int. Cl.
*A61F 2/06* (2013.01)
*A61F 2/958* (2013.01)
*A61M 25/10* (2013.01)

(52) U.S. Cl.
CPC .............. *A61F 2/958* (2013.01); *A61M 25/104* (2013.01); *A61M 25/1011* (2013.01)

(58) Field of Classification Search
CPC .. A61F 2/958; A61M 25/104; A61M 25/1011

USPC .................... 623/1.11, 1.12, 1.23, 1.15, 1.42; 606/194, 198; 604/96.01, 604/101.01–101.05

See application file for complete search history.

(56) References Cited

U.S. PATENT DOCUMENTS

| | | | |
|---|---|---|---|
| 5,226,889 A * | 7/1993 | Sheiban | 604/103.1 |
| 5,728,068 A | 3/1998 | Leone et al. | |
| 5,851,210 A * | 12/1998 | Torossian | 606/108 |
| 8,021,420 B2 | 9/2011 | Dolan | |
| 2004/0059290 A1 | 3/2004 | Palasis | |
| 2005/0251193 A1* | 11/2005 | Lary | 606/192 |
| 2006/0178721 A1 | 8/2006 | Durcan et al. | |
| 2011/0040319 A1 | 2/2011 | Fulton, III | |
| 2011/0160647 A1* | 6/2011 | Tsukashima et al. | 604/22 |

FOREIGN PATENT DOCUMENTS

JP 2009-247506 A 10/2009

* cited by examiner

*Primary Examiner* — Katrina Stransky

(74) *Attorney, Agent, or Firm* — Buchanan Ingersoll & Rooney PC (57) ABSTRACT

Disclosed herein is a stent delivery system which includes: a hollow shaft; first and second expandable balloons arranged around of the distal end of the shaft; and a stent which is arranged around the second balloon such that it expands as the second balloon expands; the first balloon having drug release means for releasing a drug at least to prevent the proliferation of endothelial cells, the stent being a bare metal stent to be indwelled at a target position as lesion of stenosis or occlusion in the lumen of a living body.

4 Claims, 14 Drawing Sheets

STENT DELIVERY SYSTEM AND METHOD USING THE SAME

This application is a divisional of U.S. application Ser. No. 13/401,185 filed on Feb. 21, 2012, which claims priority of JP 2011-066755 filed in Japan on Mar. 24, 2011, the disclosure of the prior applications is hereby incorporated by reference herein in their entirety.

TECHNICAL FIELD

Background Discussion

A stent delivery system is a known medical tool used to deliver a stent to cure legions (such as stenosis and occlusion) occurring in the lumen of a living body. The stent delivery system is composed of a hollow shaft, a balloon arranged around the distal end of the shaft, and a stent such that the balloon expands to expand the stent.

Current treatment with a stent mostly involves a DES (Drug Eluting Stent) which is designed to prevent the proliferation of endothelial cells by the drug effect, thereby curing restenosis at the legion after operation. An example is disclosed in Japanese Patent Laid-Open No. 2009-247506.

The drug eluting stent has a possibility of causing the delayed stent thrombosis which appears after about one year following placement of the stent, or later. A clinical way of reducing this risk is by long-term administration of an antiplatelet drug. The drug eluting stent may be replaced by a bare metal stent (BMS) made of metal alone to reduce the possibility of the delayed stent thrombosis occurring; however, the latter has the disadvantage of causing restenosis more frequently than the former.

SUMMARY

The stent delivery system disclosed here is composed of a hollow shaft, first and second expandable balloons arranged around the distal end of the shaft, and a stent which is arranged around the second balloon such that it expands as the second balloon expands. The first balloon has drug release means for releasing a drug at least to prevent the proliferation of endothelial cells and the stent is a bare metal stent to be indwelled at a target position as the lesion of stenosis or occlusion in the lumen of a living body.

According to another aspect a stent delivery system includes: a longitudinally extending hollow shaft; a first balloon possessing surrounding a distal end portion of the shaft so that the distal end portion of the shaft passes through the first balloon, with the first balloon being expandable upon introducing fluid into the interior of the first balloon; and a second balloon spaced apart from the first balloon along a longitudinal extent of the shaft, wherein the second balloon surrounds the distal end portion of the shaft so that the distal end portion of the shaft passes through the second balloon, and wherein the second balloon is expandable upon introducing fluid into the interior of the second balloon. The shaft includes a first lumen which opens into the interior of the first balloon to introduce the fluid into the interior of the first balloon to expand the first balloon and cause the first balloon to apply an expansion force to a target site in a lumen of a living body, and a second lumen which opens into the interior of the second balloon to introduce the fluid into the interior of the second balloon to expand the second balloon and cause the second balloon to apply an expansion force to the target site in the lumen of the living body. The first balloon comprises drug release means for releasing a drug which inhibits proliferation of endothelial cells, and a metal stent surrounds the second balloon and is expandable upon expansion of the second balloon so that the stent contacts a surface of the target site in the lumen of the living body. The metal stent is devoid of any drug which inhibits proliferation of endothelial cells.

Another aspect involves a method for placing a stent at a target site in a living body. The method involves inserting the distal end of a hollow shaft of a stent delivery system into the lumen of a living body, wherein the stent delivery system also comprises first and second axially spaced apart expandable balloons arranged around the distal portion of the shaft, and a stent arranged around the second balloon to expand together with expansion of the second balloon. The method further involves moving the shaft to position the first balloon at a target site in the lumen of the living body, expanding the first balloon, delivering to the target site a drug which at least inhibits proliferation of endothelial cells, with the drug being delivered to the target site by way of the expanded first balloon while the first balloon is positioned at the target site, collapsing the first balloon, moving the shaft after collapsing the first balloon to position the stent at the target site at which the drug was delivered, expanding the second balloon to expand the stent so that the stent comes into contact with a surface of the target site, collapsing the second balloon, and withdrawing the shaft, together with the first and second balloons, from the body lumen of the living body while the stent remains in contact with the surface of the target site.

The stent delivery system includes the first balloon provided with the drug releasing means which releases a drug to prevent the proliferation of endothelial cells, thereby reducing the possibility of restenosis occurring at the target position. Moreover, it has a bare metal stent as an indwelling stent, so that it reduces the possibility of delayed stent thrombosis occurring. The stent delivery system that reduces the possibilities of restenosis and delayed stent thrombosis occurring.

The drug releasing means may be a drug-covering layer arranged around the first balloon or openings arranged around the first balloon such that it releases the drug supplied through the lumen of the shaft.

The first balloon should preferably be positioned ahead of (distally beyond) the stent. This permits the pre-expansion of the first balloon at the target position and the smooth placement of the stent that follows the balloon expansion.

The stent delivery system may have a third expandable balloon arranged around the distal of the shaft. In this case, the third expandable balloon relatively easily permits the post-expansion of the indwelled stent, which obviates the necessity of the balloon catheter for post-expansion.

The stent should preferably be positioned near the tip of the third balloon to help ensure smooth stent placement and ensuing post-expansion.

The drug to prevent the proliferation of endothelial cells may be sirolimus or paclitaxel.

The drug to prevent the proliferation of endothelial cells may also be supplemented with a drug to cure the target position (such as hypolipidemic drug).

DETAILED DESCRIPTION

Referring initially to FIGS. 1-4, a stent delivery system 100 according to one embodiment disclosed here by way of example is used in connection with curing stenosis or occlusion that occurs in the lumen of a living body, which includes blood vessel, bile duct, trachea, esophagus, and urethra. One object of curing stenosis is to prevent restenosis that occurs after PCI (Percutaneous Coronary Intervention).

Figure 1:
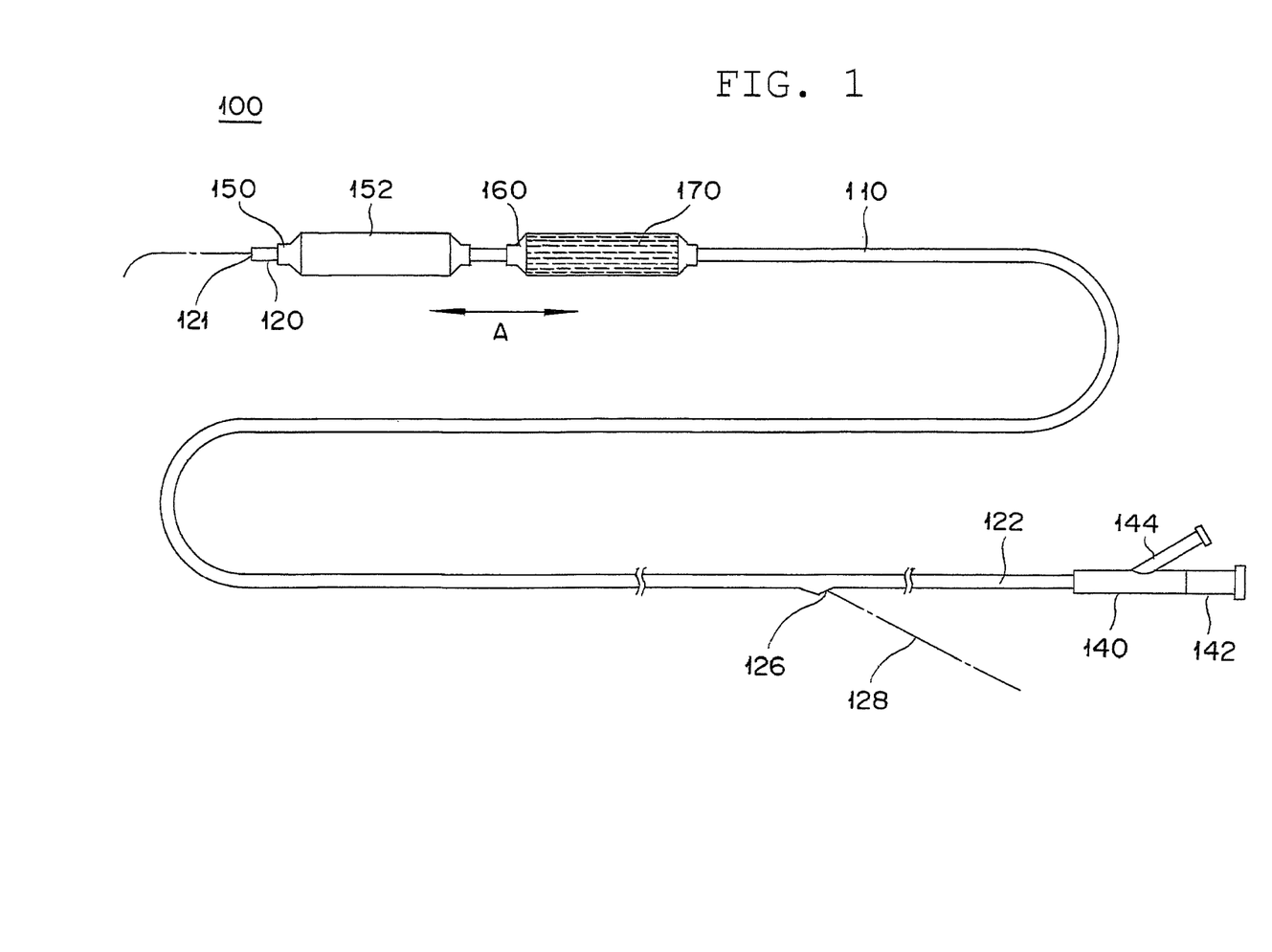
FIG. 1 is a side view illustrating the stent delivery system according to one embodiment disclosed here by way of example.

The stent delivery system 100 is of rapid exchange type (RX) as shown in FIG. 1. It is composed of a hollow shaft 110, first and second balloons 150 and 160, which are arranged around the shaft 110, and a stent 170 arranged around or encircling the second balloon 160.

The shaft 110 is composed of a distal end 120 around which the first and second balloons 150 and 160 are arranged, a base shaft 122 on which a guide wire port 126 is formed, and a hub 140 which is attached to the proximal end of the base shaft 122.

Figure 3:
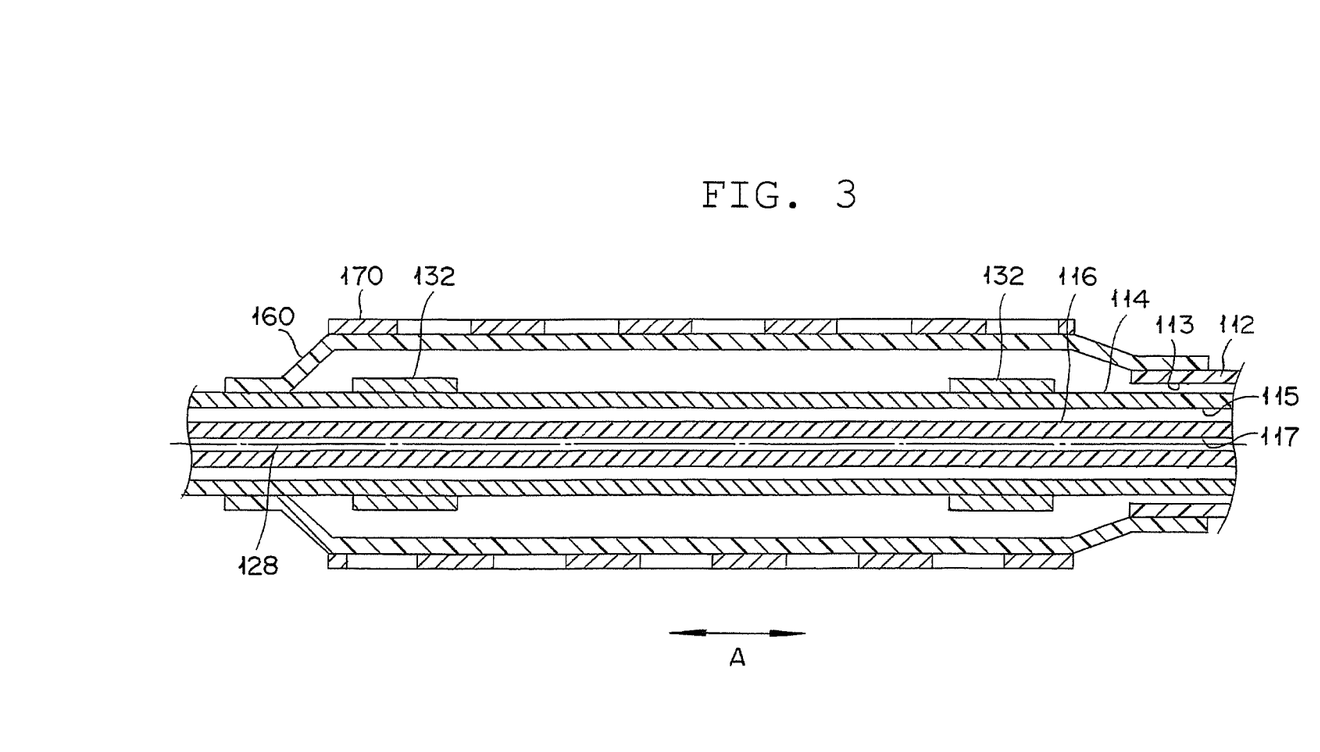
FIG. 3 is a longitudinal cross-sectional view of the stent shown in FIG. 1.

The shaft 110 is a multilayered tube as shown in FIG. 3. That is, it is composed of an outer tube 112, an inner tube 114 which extends inside the outer tube 112, and a central tube 116 which extends inside the inner tube 114.

A space exists between the inner surface of the outer tube 112 and the outer surface of the inner tube 114. This space functions as an expanding lumen 113, which communicates with the second balloon 160 and a second expanding port 144 and serves for introduction and discharge of a pressurized fluid to expand the second balloon 160. A space also exists between the inner surface of the inner tube 114 and the outer surface of the central tube 116. This space functions as an expanding lumen 115 (shown in FIGS. 2 and 3), which communicates with the first balloon 150 and a first expanding port 142 and serves for introduction and discharge of a pressurized fluid to expand the first balloon 150. The pressurized fluid is physiological saline, contrast medium for blood vessels, and the like. In this disclosed embodiment disclosed by way of example, the two expanding lumens 113, 115 are configured to permit the first and second balloons 150, 160 to be inflated or expanded independent of one another, meaning that the fluid introduced passing through one of the lumens 113, 115 to expand one of the balloons 150, 160 does not also expand the other balloon.

A guide wire lumen 117 (shown in FIG. 2), which extends inside the central tube 116, communicates with a distal tip 121 of the hollow shaft 110 and the guide wire port 126. It permits a guide wire 128 to project beyond the distal end 120.

The passage for introduction and discharge of the pressurized fluid into and from the first and second balloons 150 and 160 is not limited to the mode in which the passage is defined by the space existing between inner wall and outer wall of multilayer tube.

The outer tube 112 should preferably be made of an elastic material such as thermoplastic resin and rubber. The former includes polyethylene, polypropylene, polybutene, ethylene-propylene copolymer, ethylene-vinyl acetate copolymer, ionomer, polyolefin composed of two or more of the species, soft polyvinyl chloride resin, polyamide, polyamide elastomer, polyester, polyester elastomer, polyurethane, and fluoroplastics. The latter includes silicone rubber and latex rubber.

The inner tube 114 and the central tube 116 may be formed from the same material as the outer tube 112 or a metallic material such as stainless steel, extensible stainless steel alloy, and Ni—Ti alloy.

The hub 140 may be formed from plastics such as polycarbonate, polyolefin, styrene resin, and polyester, stainless steel, aluminum, aluminum alloy, or the like.

The inner tube 114 and central tube 116 have coil markers 132 and 134, which are made of an X-ray opaque material. The markers 132 (shown in FIG. 3) are arranged around the outer surface of the inner tube 114 in such a way that their position coincides with both ends of the stent 170 (and the second balloon 160). The markers 134 (shown in FIG. 2) are arranged around the central tube 116 in such a way that their position coincides with both ends of the first balloon 150.

The markers 132 and 134 produce sharp images for X-ray radioscopy, so that the operator can rather easily recognize the position of the distal end 120 of the shaft 110 or the position of the first balloon 150 and the stent 170. The number and position of the markers 132 and 134 may be properly changed, or the markers 132 and 134 may be omitted according to need.

The markers 132 and 134 may be formed from an X-ray opaque material selected from platinum, tantalum, iridium, rhenium, tungsten, palladium, rhodium, silver, ruthenium, and hafnium, or alloys thereof.

The markers 132 and 134 may be either X-ray opaque or ultrasonic opaque. The markers 132 and 134 may be fixed to the inner tube 114 and the central tube 116 in any way, such as staking, welding, and bonding.

The first balloon 150 is of the DEB (Drug Eluting Balloon) type. The first balloon 150 has a covering layer 152 coated with a drug to prevent the proliferation of endothelial cells, so that it releases a drug. The covering layer 152 is an example of a drug-release means for releasing the drug at a desired site in the living body to at least inhibit proliferation of endothelial cells. The drug to be released should preferably be difficultly soluble or insoluble in water so that it does not dissolve in blood. The covering layer 152 may be formed in any way without specific restrictions. Possible ways include transfer, dipping, and spraying. The covering layer 152 may also contain a supplementary drug such as antihyperlipidemic drug to cure the target position as lesions such as stenosis or occlusion.

Figure 2:
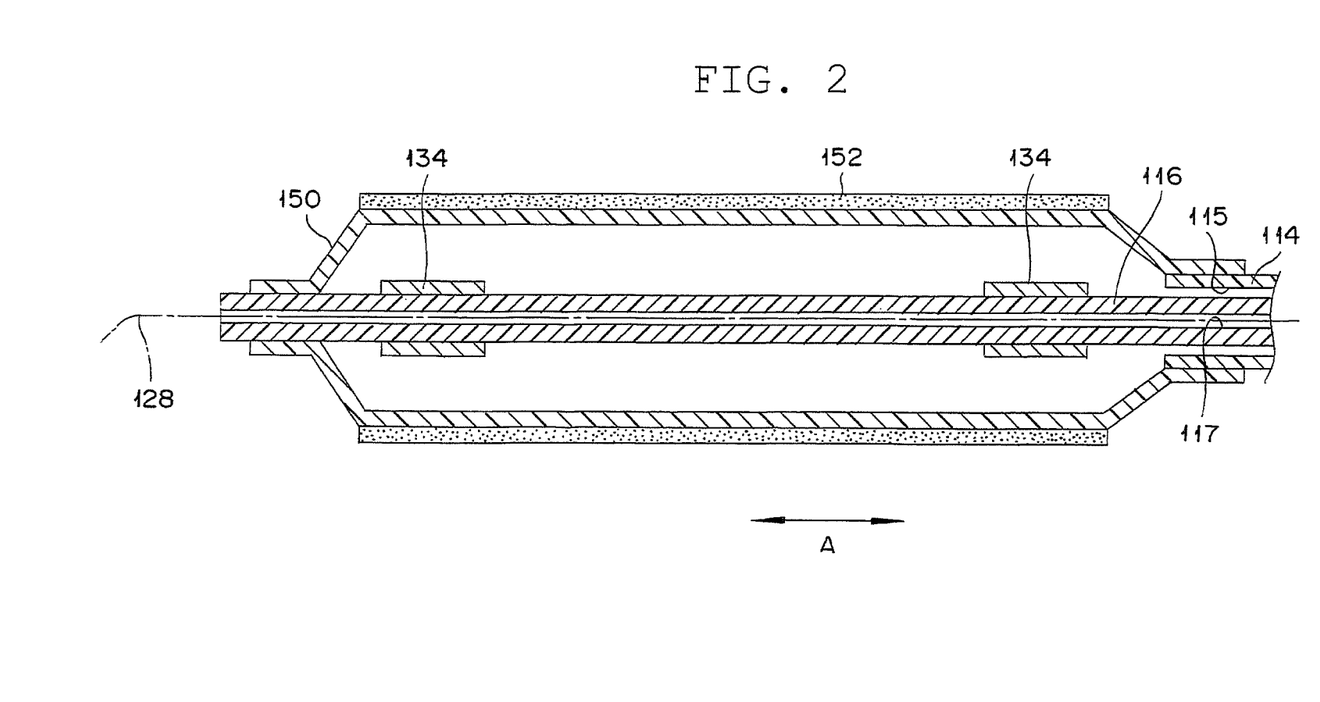
FIG. 2 is a longitudinal cross-sectional view of the first balloon shown in FIG. 1.

The first balloon 150 is arranged in the axial direction around the distal end 120 of the shaft 110 (as shown in FIG. 2). The first balloon communicates with the first expanding port 142 through the expanding lumen 115 (as shown in FIGS. 2 and 3). Therefore, the first balloon 150 expands as the pressurized fluid is introduced by way of the first expanding port 142. Upon expansion, the first balloon 150 permits the covering layer 152 arranged around it to come into close contact with the target position, so that the drug carried by the covering layer 152 is transferred to the target position.

The drug prevents the proliferation of endothelial cells, thereby reducing the possibility of restenosis occurring at the target position. The first balloon 150 collapses after drug release and moves away from the target position. Therefore, the stent delivery system of the present invention does not cause irritation continuously for a long period of time, unlike the conventional indwelling drug eluting stent.

Moreover, the first balloon 150, which is devoid of any stent, performs pre-expansion at the target position of the lesion when it releases the drug, and this obviates the necessity for the balloon catheter for pre-expansion. Being positioned toward the distal end away from the stent 170, the first balloon 150 permits smooth pre-expansion and subsequent smooth placement of the stent 170.

The drug to be contained in the covering layer 152 includes, for example, anticancer drug, immunosuppresive drug, antibiotic, antirheumatic drug, antithrombotic drug, HMG-CoA reductase inhibitor, insulin resistance improver, ACE inhibitor, calcium antagonist, antihyperlipidemic drug, integrin inhibitor, antiallergic drug, antioxidant, GP IIb/IIIa antagonist, retinoid, flavonoid, carotenoid, lipid improver, DNA synthesis inhibitor, tyrosine kinase inhibitor, antiplatelet drug, antiinflammatory drug, tissue-derived biomaterial, interferon, and nitrogen monoxide generation promoting substance.

The anticancer drug includes, for example, vincristine, vinblastine, vindesine, irinotecan, pirarubicin, paclitaxel, docetaxel, and methotrexate. The immunosuppresive drug includes, for example, sirolimus and derivatives thereof, such as everolimus, pimecrolimus, ABT-578, AP23573, and CCI-779; tacrolimus, azathioprine, ciclosporin, cyclophosphamide, mycophenolate mofetil, gusperimus, mizoribine, and doxorubicin.

The antibiotic includes, for example, mitomycin, actinomycin, daunorubicin, idarubicin, pirarubicin, aclarubicin, epirubicin, peplomycin, and zinostatin stimalamer. The antirheumatic drug includes, for example, methotrexate, sodium thiomalate, penicillamine, and lobenzarit. The antithrombotic drug includes, for example, heparin, aspirin, antithrombin drug, ticlopidine, and hirudin.

The HMG-CoA reductase inhibitor includes, for example, cerivastatin, cerivastatin sodium, atorvastatin, atorvastatin calcium, rosuvastatin, rosuvastatin calcium, pitavastatin, pitavastatin calcium, fluvastatin, fluvastatin sodium, simvastatin, lovastatin, pravastatin, and pravastatin sodium.

The insulin resistance improver includes, for example, thiazolidine derivatives, such as troglitazone, rosiglitazone, and pioglitazone. The ACE inhibitor includes, for example, quinapril, perindopril erbumine, trandolapril, cilazapril, temocapril, delapril, enalapril maleate, lisinopril, and captopril. The calcium antagonist includes, for example, nifedipine, nilvadipine, diltiazem, benidipine, and nisoldipine.

The antihyperlipidemic drug includes, for example, bezafibrate, fenofibrate, ezetimibe, torcetrapib, pactimibe, K-604, implitapide, and probucol.

The integrin inhibitor includes, for example, AJM300. The antiallergic drug includes, for example, tranilast. The antioxidant includes, for example, α-tocopherol, catechin, dibutylhydroxytoluene, and butylhydroxyanisol. The GP IIb/IIIa antagonist includes, for example, abciximab. The retinoid includes, for example, all-trans retinoic acid. The flavonoid includes, for example, epigallocatechin, anthocyanin, and proanthocyanidin. The carotenoid includes, for example, β-carotene and lycopene.

The lipid improver includes, for example, eicosapentaenoic acid. The DNA synthesis inhibitor includes, for example, 5-FU. The tyrosine kinase inhibitor includes, for example, genistein, tyrphostin, erbstatin, and staurosporine. The antiplatelet drug includes, for example, ticlopidine, cilostazol, and clopidogrel. The antiinflammatory drug includes, for example, such steroid as dexamethasone and prednisolone.

The tissue-derived biomaterial includes, for example, EGF (epidermal growth factor), VEGF (vascular endothelial growth factor), HGF (hepatocyte growth factor), PDGF (platelet derived growth factor), and BFGF (basic fibroblast growth factor). The interferon includes, for example, interferon-γ1a. The nitrogen monoxide generation promoting substance includes, for example, L-arginine.

Of these drugs, the following are preferable in view of the fact that they are commonly used to cure stenosis and they rapidly migrate into cells. Paclitaxel, docetaxel, sirolimus and everolimus. The first and third ones are most desirable.

The second balloon 160 is arranged in the axial direction A around the distal end portion 120 of the shaft 110, as shown in FIG. 3, and is proximally positioned relative to the first balloon 150. The second balloon 160 communicates with the second expanding port 144 through the expanding lumen 133, so that it expands upon introduction of the pressurized fluid from the second expanding port 144, thereby expanding the stent 170 arranged around it.

The first and second balloons 150 and 160 may be formed from any one of polyolefin such as polyethylene, polypropylene, ethylene-propylene copolymer, ethylene-vinyl acetate copolymer, and crosslinked ethylene-vinyl acetate copolymer, polyvinyl chloride, polyamide elastomer, polyurethane, polyester such as polyethylene terephthalate, polyarylenesulfide such as polyphenylenesulfide, silicone rubber, and latex rubber.

Figure 4:
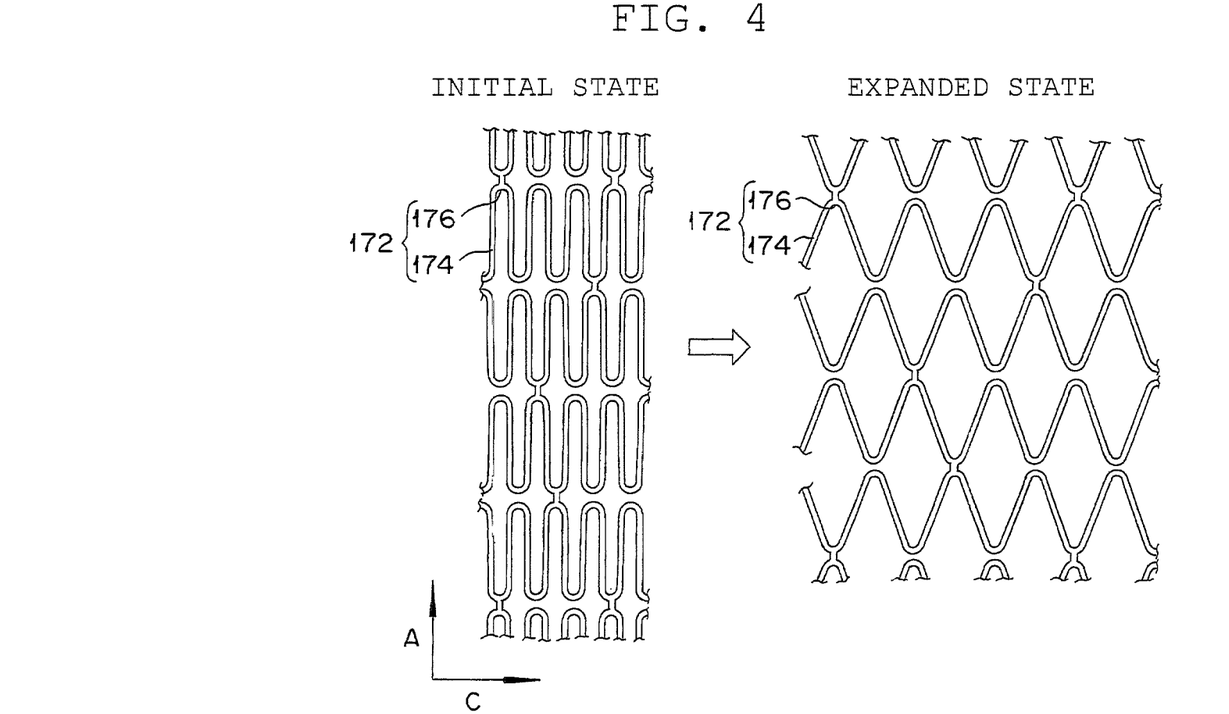
FIG. 4 is a plan view of the stent in an initial state and an expanded state.

The stent 170 is a bare metal stent made of metal alone. The stent is thus uncoated and is devoid of any drug which inhibits or prevents the proliferation of endothelial cells. It is constructed of a plurality of wavy struts 172 arranged side by side in the axial direction A, as shown in FIG. 4. Each wavy strut 172 has straight parts 174 and apexes 176 at which the straight part 174 is folded back. Each wavy strut 172 is annularly shaped, extending (to make one turn) in the circumferential direction C of the stent 170. In addition, the axially adjacent wavy struts 172 are joined together at their spaced apart or intermittently separate apexes 176, so that the axially arranged annular struts 172 as a whole form a cylindrical structure configured to expand and contract in the radial direction.

The covering layer 152 on the first balloon 150 should preferably be longer than the stent 170 in its axial direction for the following reason. The first balloon 150 achieves the pre-expansion of the target position, and then it is moved in the distal direction, whereupon the stent 170 is indwelled at the position where the first balloon 150 released the drug. This effectively prevents restenosis.

The stent 170 expands outwardly by plastic deformation as the second balloon 160 located inside the stent 170 expands outwardly. After the stent 170 has come into close contact with the target position, the second balloon 160 is collapsed so that the stent 170 separates from the second balloon 160. In other words, the stent 170, which does not have a drug releasing function, is indwelled at the target position, and this reduces the possibility of inducing delayed stent thrombosis.

This produces the effect of shortening the period for administration of a drug to inhibit or prevent stent thrombosis. Moreover, the stent 170 does not require complicated manufacturing process for one-side coating that enables drug release.

The stent 170 may be formed from any metallic material compatible with the living body, such as nickel-titanium alloy, cobalt-chromium alloy, platinum-chromium alloy, stainless steel, iron, titanium, aluminum, tin, zinc-tungsten alloy, magnesium, and magnesium alloy.

The wavy strut 172 may be formed in any way without specific restrictions. For example, it may be formed from a cylindrical stock by laser cutting according to the pattern of the wavy strut 172 or by etching with the help of a mask corresponding to the pattern of the wavy strut 172. There are other possible ways of making the stent 170 so that it is configured to be expandable and contactable in its radial direction.

Referring to FIGS. 5-11, the following is a detailed description of a manner of using the stent delivery system.

The usage of the stent delivery system 100 generally involves a balloon positioning step, a pre-extension step, a balloon collapsing step, a stent positioning step, a stent expansion step, a stent placement step, and a retracting step.

Figure 5:
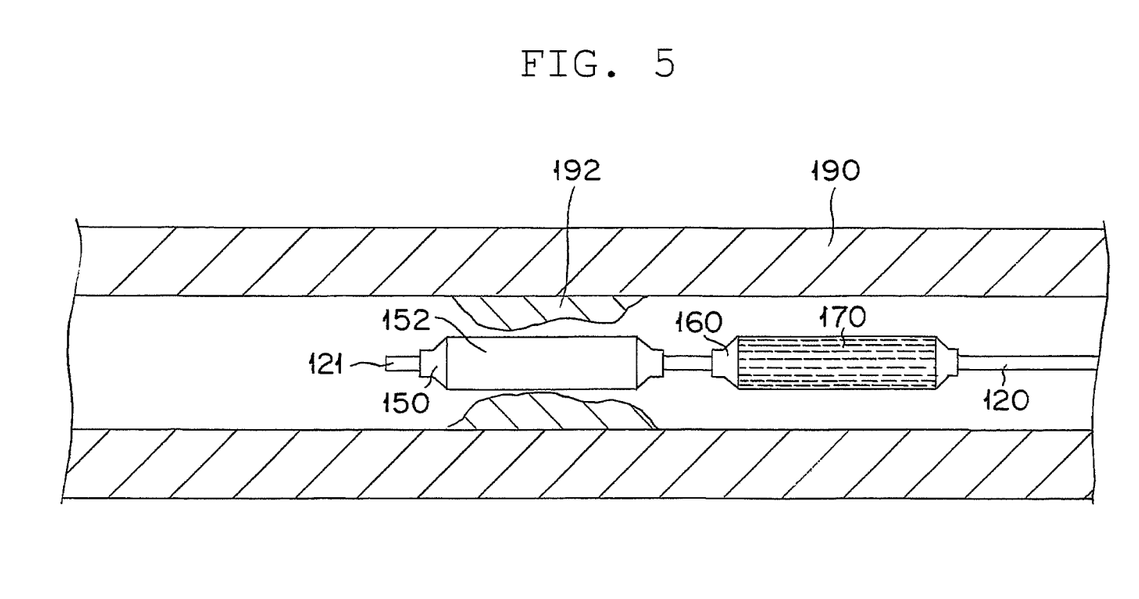
FIG. 5 is a longitudinal cross-sectional view of the balloon positioning step in the operation of the stent delivery system.

The balloon positioning step involves placing the first balloon 150 at a stenotic part 192 by inserting the distal end 120 of the shaft 110 into a patient's lumen 190, with the guide wire 128 (projecting distally beyond the distal tip 121) preceding, as shown in FIG. 5. The positioning can be accomplished accurately, easily, and rapidly by visually recognizing under X-ray radioscopy the markers 134 (shown in FIG. 2) which are aligned with both ends of the first balloon 150.

Figure 6:
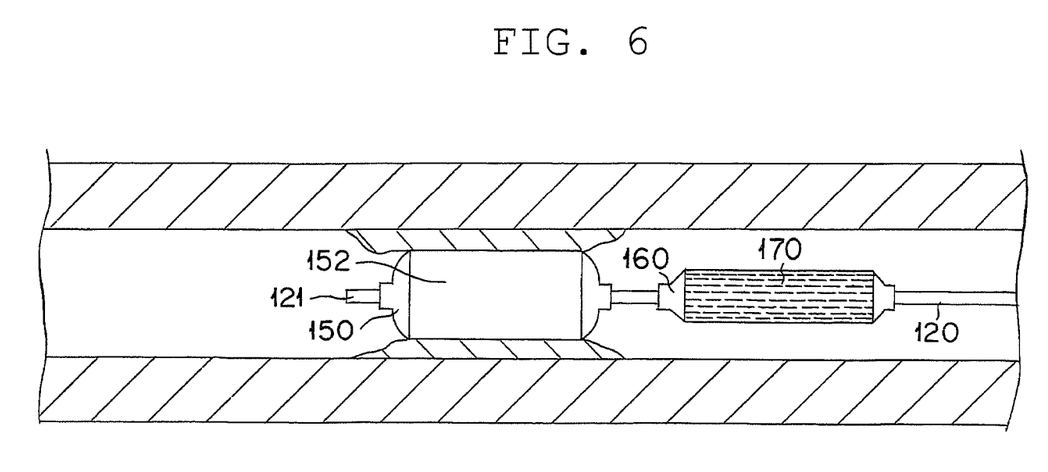
FIG. 6 is a longitudinal cross-sectional view of the pre-expansion step that follows the step shown in FIG. 5.

In the pre-expansion step, after the first balloon 150 is located at the stenotic part 192, a pressurized fluid is introduced from the first expanding port 142, through the expanding lumen 115, and into the first balloon 150 to radially outwardly expand the first balloon 150. The first balloon 150, which has been expanded, causes the covering layer 152 which surrounds the first balloon 150 to come into close contact with the stenotic part 192, so that the drug constituting the covering layer 152 transfers to the stenotic part 192, and the stenotic part 192 is expanded (for pre-expansion), as shown in FIG. 6.

Figure 7:
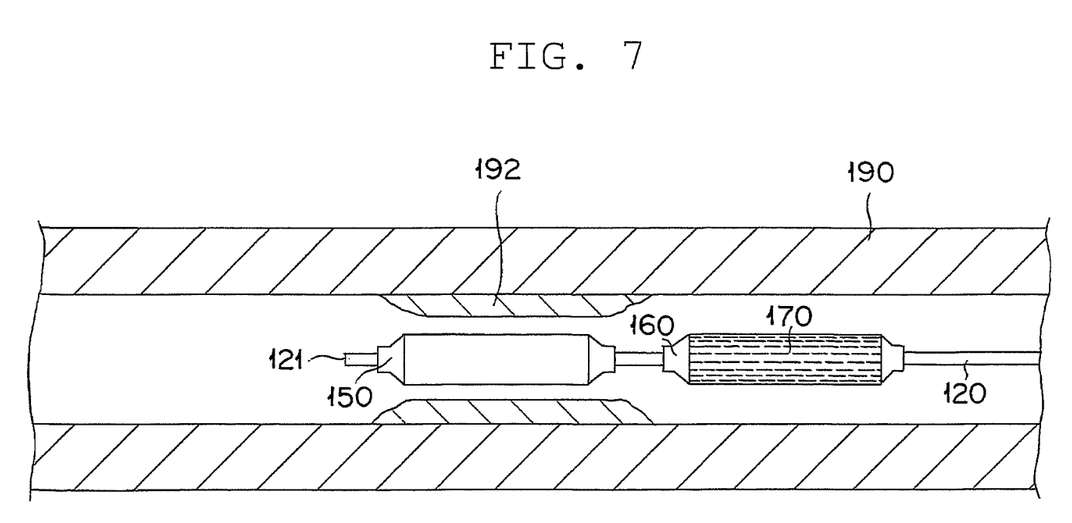
FIG. 7 is a longitudinal cross-sectional view of the balloon collapsing step that follows the step shown in FIG. 6.

In the balloon collapsing step, the pressurized fluid is discharged from the first expanding port 142 through the expanding lumen 115, so that the first balloon 150 collapses, as shown in FIG. 7. After the first balloon 150 has collapsed, the stenotic part 192 remains expanded.

Figure 8:
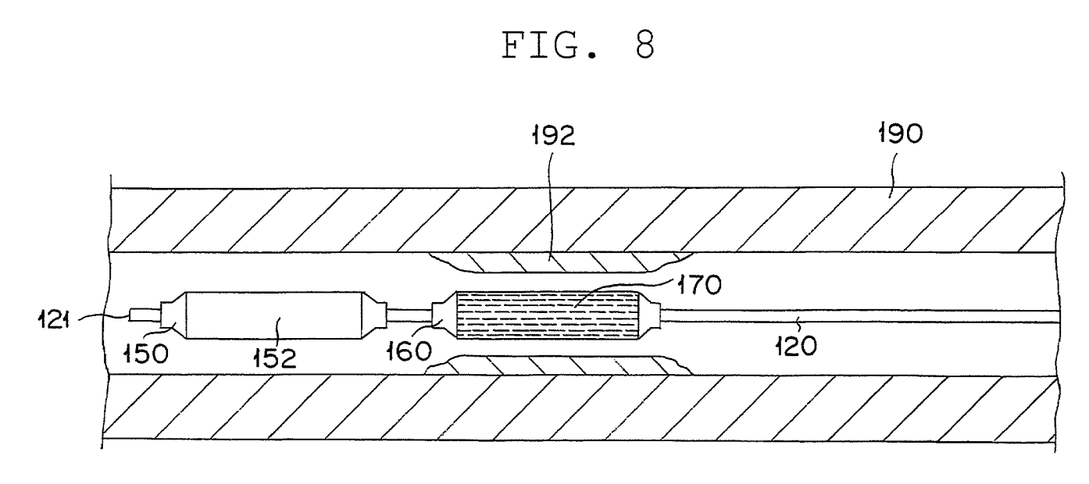
FIG. 8 is a longitudinal cross-sectional view of the stent positioning step that follows the step shown in FIG. 7.

The stent positioning step involves moving the distal end 120 of the shaft 110 (distally moving the shaft 110) to further advance or move the stent in the distal direction, thereby positioning the stent 170 at the stenotic part 192, as shown in FIG. 8. The positioning can be accomplished accurately, easily, and rapidly by visually recognizing under X-ray radioscopy the markers 132 (shown in FIG. 3) which are aligned with both ends of the stent 170.

Figure 9:
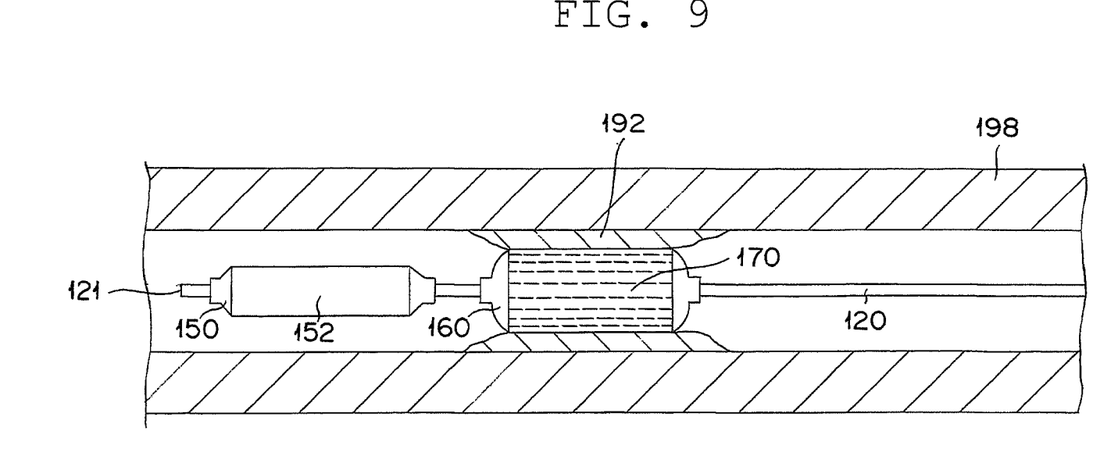
FIG. 9 is a longitudinal cross-sectional view of the stent expanding step that follows the step shown in FIG. 8.

In the stent expanding step, a pressurized fluid is introduced, by way of the second expanding port 144 and the expanding lumen 113, into the second balloon 160 to radially outwardly expand the second balloon 160. The second balloon 160, which has been radially outwardly expanded, expands the stent 170 arranged around or surrounding the second balloon 160, so that the stent 170 comes into close contact with the surface of the stenotic part 192, as shown in FIG. 9.

Figure 10:
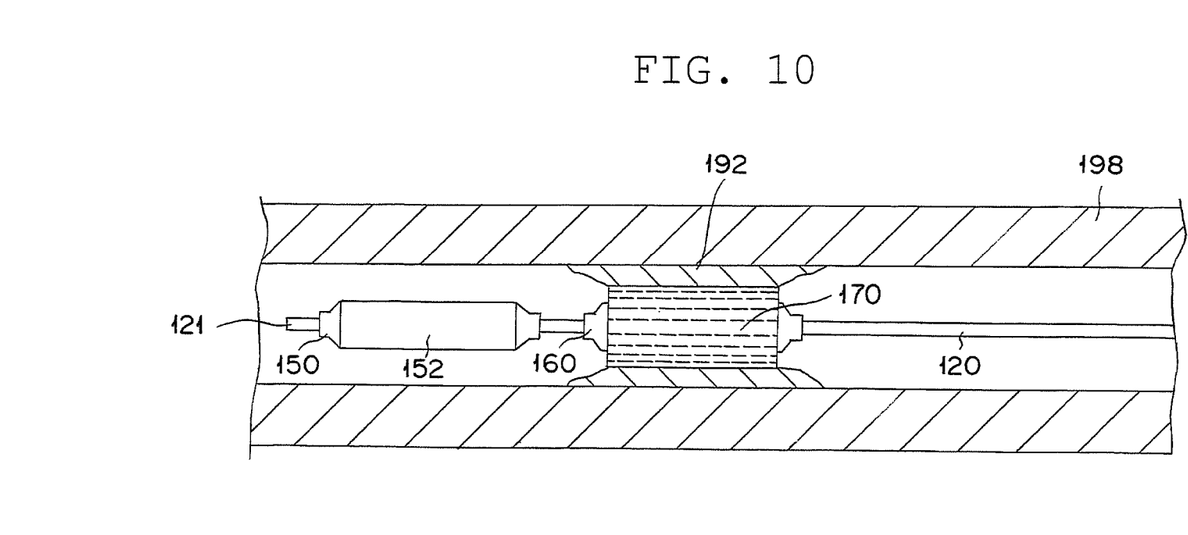
FIG. 10 is a longitudinal cross-sectional view of the stent indwelling step that follows the step shown in FIG. 9.

During the stent indwelling step, the pressurized fluid is discharged from the second expanding port 144 through the expanding lumen 113, so that the second balloon 160 collapses, as shown in FIG. 10. The collapsing of the second balloon 160 does not collapse the stent 170, which has undergone plastic deformation. In this way, the stent 170 separates from the second balloon 160.

Figure 11:
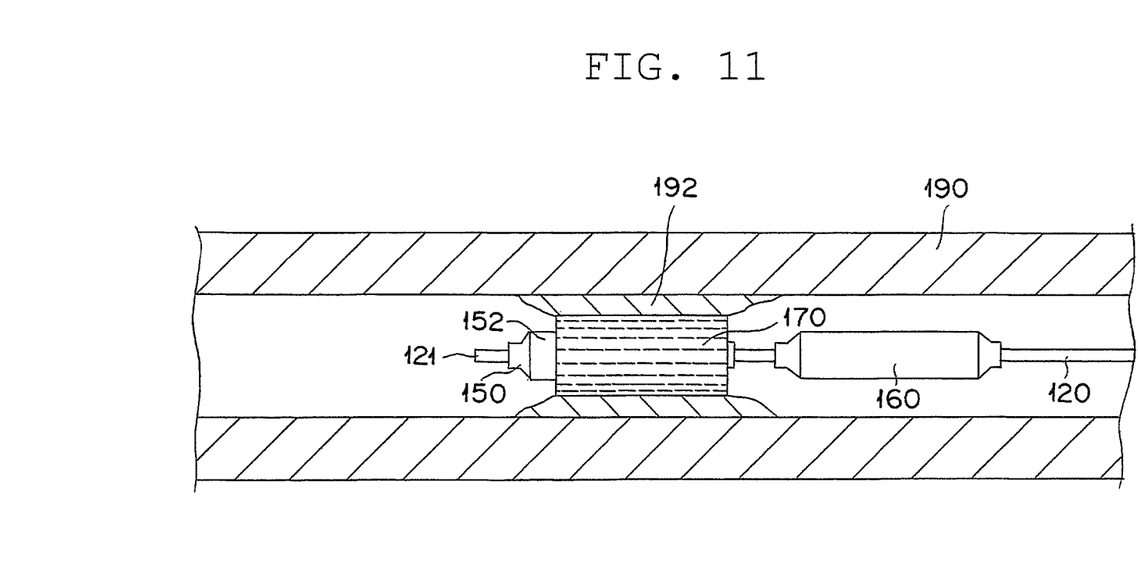
FIG. 11 is a longitudinal cross-sectional view of the retracting step that follows the step shown in FIG. 10.

The retracting step causes the distal end 120 of the shaft 110 from which the stent 170 has been separated to withdraw from the lumen 190, as shown in FIG. 11. In this way, the stent 170, which has no ability to release the drug, is indwelled in the stenotic part 192.

Figure 12:
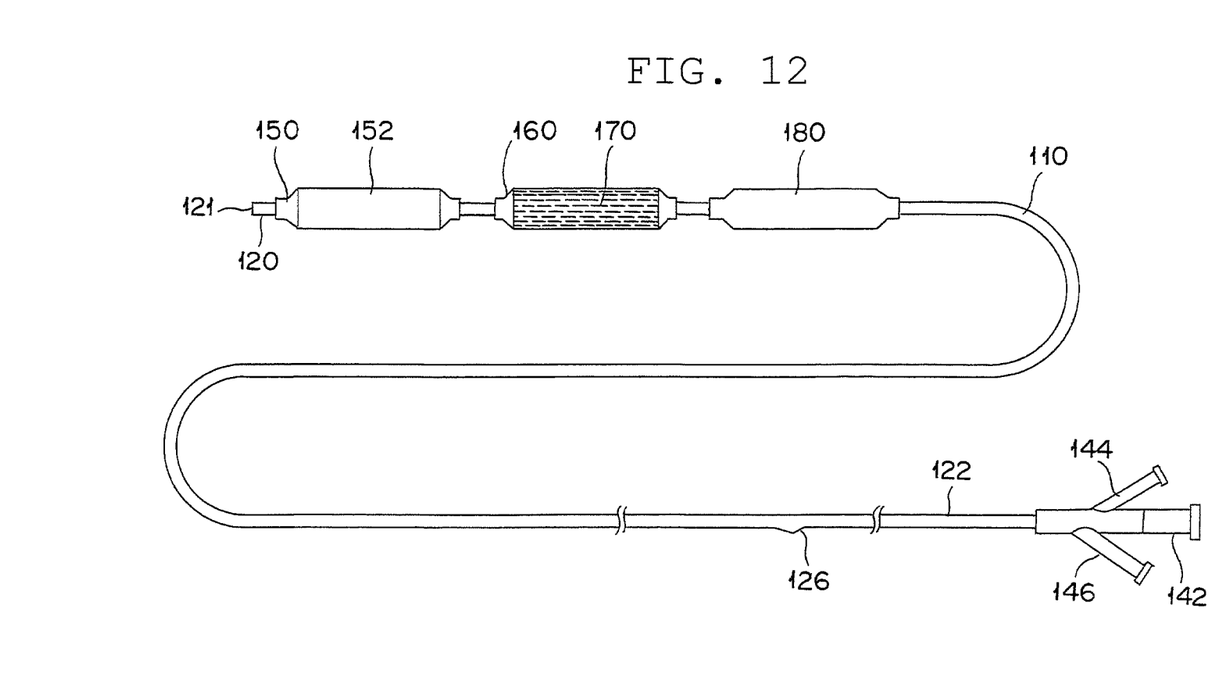
FIG. 12 is a side view of a modified embodiment of the stent delivery system disclosed by way of example.
Figure 13:
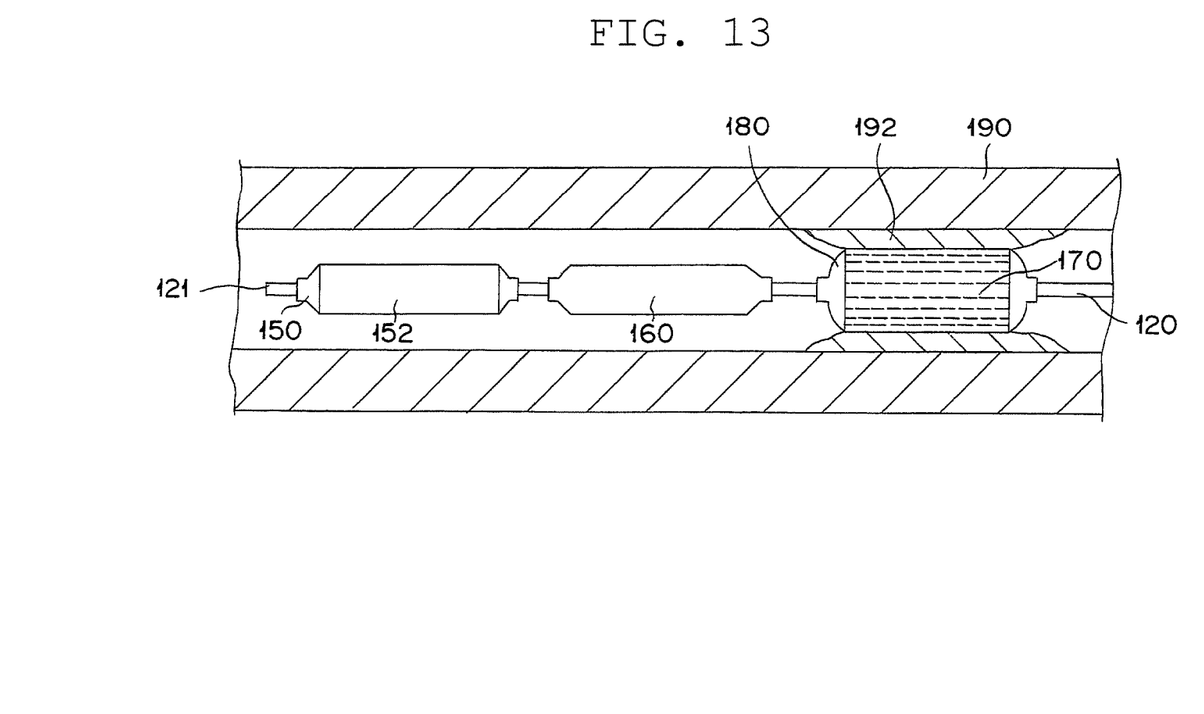
FIG. 13 is a longitudinal cross-sectional view of the post-expanding step involved in the modified embodiment of the stent delivery system shown in FIG. 12.

FIGS. 12 and 13 illustrate a modified version of the stent delivery system disclosed by way of example. According to this modified example, the stent delivery system 100 includes a third balloon 180, which relatively easily performs post-expansion of the stent 170 which has been indwelled, thereby eliminating the necessity for the balloon catheter for post expansion.

In other words, the stent delivery system 100 is constructed such that the third balloon 180 is arranged closer to the proximal end (i.e., the third balloon is more proximal) than the second balloon 160, and communicates with a third expanding port 146 attached to the hub. The third balloon 180 executes the post-expansion step between the stent placement step and the retracting step.

In the post-expansion step, the third balloon 180 is inserted into the stent 170 which has been indwelled at the stenotic part 192 by the second balloon 160, and then a pressurized fluid is introduced from the third expanding port 146 to radially outwardly expand the third balloon 180. Thus, the stent 170 is expanded again (for post expansion). The placement of the stent 170 and the ensuing post expansion can be carried out relatively smoothly because the stent 170 is positioned closer to the distal end than the third balloon 180.

Figure 14:
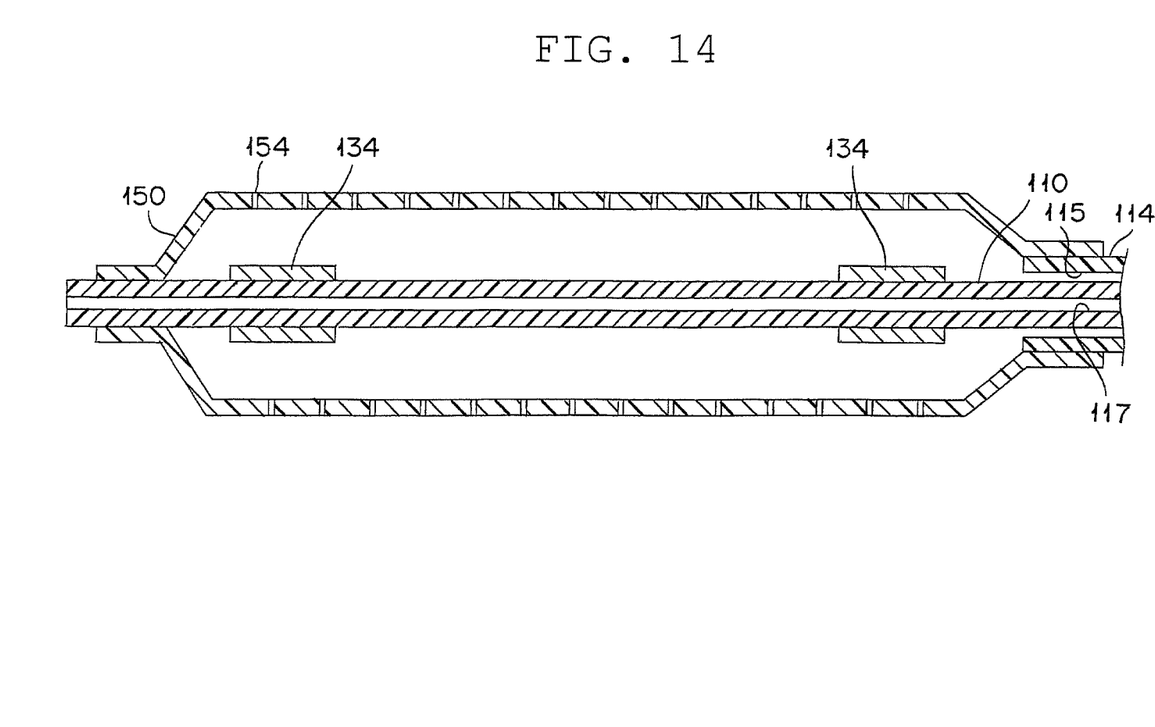
FIG. 14 is a side view of another modified embodiment of the stent delivery system disclosed by way of example.

FIG. 14 illustrates another modified version of the stent delivery system disclosed by way of example. According to this modified example, the application of a drug to the surface of the stenotic part 192 is carried out differently than resorting to the covering layer 152 coated with a drug. This is achieved by introducing a pressurized fluid containing the desired drug from the first expanding port 142 and delivering it to through openings or holes 154 which are arranged around the first balloon 150 and which communicate with the expanding lumen 115. In this case, the drug flows or passes through the through openings 154 and reaches the surface of the stenotic part 192. The through holes or openings 154 represent another example of a drug-release means for releasing the drug at a desired site in the living body to at least inhibit proliferation of endothelial cells.

The stent delivery system disclosed here offers the advantage that the drug released from the drug releasing means arranged on the first balloon inhibits or prevents the proliferation of endothelial cells and hence reduces the possibility of restenosis occurring at the target position. Moreover, the indwelled stent is composed of a bare metal stent, so that it reduces the possibility of delayed stent thrombosis occurring. The stent delivery system is thus able to reduce the possibility of restenosis and delayed stent thrombosis occurring.

The stent delivery system described above by way of several embodiments disclosed by way of example is a rapid exchange type. But the invention is not limited in this regard. For example, the stent delivery system 100 may be applied to that of an over-the-wire (OTW) type as well as that of rapid exchange type.

The detailed description above describes features and aspects of examples of embodiments of a stent delivery system. The present invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A method for placing a stent at a target site in a living body comprising:
    inserting a distal end of a hollow shaft of a stent delivery system into the lumen of a living body, the stent delivery system also comprising first and second axially spaced apart expandable balloons arranged around a distal portion of the shaft, a third expandable balloon arranged around the shaft, and a stent arranged around the second balloon to expand together with expansion of the second balloon;
    moving the shaft to position the first balloon at a target site in the lumen of the living body;
    expanding the first balloon;
    delivering to the target site a drug which at least inhibits proliferation of endothelial cells, the drug being delivered to the target site by way of the expanded first balloon while the first balloon is positioned at the target site;
    collapsing the first balloon;
    moving the shaft after collapsing the first balloon to position the stent at the target site at which the drug was delivered;
    expanding the second balloon to expand the stent so that the stent comes into contact with a surface of the target site;
    collapsing the second balloon;
    after collapsing the second balloon, moving the shaft to position the third balloon at the target site at which is located the stent;
    expanding the third balloon so that the third balloon contacts the stent and applies an outward expansion force to the stent; and
    withdrawing the shaft, together with the first and second balloons, from the body lumen of the living body while the stent remains in contact with the surface of the target site.

2. The method according to claim 1, wherein the delivering of the drug to the target site involves pressing a covering layer which surrounds the first balloon into contact with the target site, the covering layer being coated with the drug.

3. The method according to claim 1, wherein the delivering of the drug to the target site involves conveying a pressurized fluid into the first balloon and through holes in the first balloon, the pressurized fluid including the drug.

4. The method according to claim 1, wherein the moving of the shaft after collapsing the first balloon comprises moving the shaft distally so that the collapsed first balloon is positioned distally of the target site when the second balloon is expanded to expand the stent into contact with the surface of the target site.

* * * * *